US008591406B2

(12) United States Patent
Hirayama

(10) Patent No.: US 8,591,406 B2
(45) Date of Patent: Nov. 26, 2013

(54) ENDOSCOPE EQUIPPED WITH A NOZZLE FOR CLEANING ITS DISTAL END

(75) Inventor: Tetsu Hirayama, Tokyo (JP)

(73) Assignee: Hoya Corporation, Tokyo (JP)

( * ) Notice: Subject to any disclaimer, the term of this patent is extended or adjusted under 35 U.S.C. 154(b) by 472 days.

(21) Appl. No.: 12/855,829

(22) Filed: Aug. 13, 2010

(65) Prior Publication Data
US 2011/0046446 A1   Feb. 24, 2011

(30) Foreign Application Priority Data
Aug. 20, 2009   (JP) ................. 2009-190978

(51) Int. Cl.
*A61B 1/12*   (2006.01)
(52) U.S. Cl.
USPC ............ 600/157; 600/156; 600/158; 600/169
(58) Field of Classification Search
USPC .................................... 600/156–158, 169
See application file for complete search history.

(56) References Cited

U.S. PATENT DOCUMENTS

| | | | |
|---|---|---|---|
| 4,991,565 A | | 2/1991 | Takahashi et al. |
| 5,027,791 A | | 7/1991 | Takahashi |
| 5,207,213 A | * | 5/1993 | Auhll et al. .............. 600/157 |
| 5,630,795 A | * | 5/1997 | Kuramoto et al. .......... 600/157 |
| 5,685,823 A | * | 11/1997 | Ito et al. .................. 600/157 |
| 5,733,244 A | | 3/1998 | Yasui et al. |
| 5,871,440 A | * | 2/1999 | Okada .................... 600/158 |
| 6,354,519 B1 | | 3/2002 | Kidooka et al. |
| 7,588,172 B2 | | 9/2009 | Yamamoto et al. |
| 2006/0281973 A1 | | 12/2006 | Sugita |
| 2007/0260120 A1 | * | 11/2007 | Otawara ................ 600/156 |
| 2009/0253965 A1 | * | 10/2009 | Miyamoto ............... 600/157 |

FOREIGN PATENT DOCUMENTS

| | | |
|---|---|---|
| JP | 06-237889 A | 8/1994 |
| JP | 08-243077 A | 9/1996 |
| JP | 9-201332 | 8/1997 |
| JP | 11-244221 | 9/1999 |
| JP | 2000-83890 | 3/2000 |
| JP | 2003-210388 | 7/2003 |
| JP | 3447577 | 9/2003 |
| JP | 3493998 | 2/2004 |
| JP | 2004-290457 A | 10/2004 |
| JP | 3845311 | 11/2006 |

OTHER PUBLICATIONS

Japan Office action, dated Jul. 9, 2013 along with an english translation thereof.

* cited by examiner

*Primary Examiner* — Matthew J Kasztejna
*Assistant Examiner* — Kevin G Barry, III
(74) *Attorney, Agent, or Firm* — Greenblum & Bernstein, P.L.C.

(57) ABSTRACT

An endoscope is provided having an observation port, a fluid supply pipe, a cap, a fluid ejection channel, and a direction adjustment protrusion. The observation port is provided at the distal end of the endoscope, and collects light reflected from an object. The fluid supply pipe transmits gas and/or liquid to the distal end. The cap blocks the distal end of the fluid supply pipe and is configured so that a partially enclosed semispherical space is created between the distal end of the fluid supply pipe and the inner surface of the cap. The fluid ejection channel has an outlet in the direction of the observation port, and extends from the edge of the opening at the distal end of the fluid supply pipe to the outlet and occupies the semispherical space inside the cap. The direction adjustment protrusion extends over the outlet in the lengthwise direction of the fluid ejection channel. When the outlet is projected outward toward the observation port, the plane of projection is parallel to the outlet and its lengthwise direction is parallel to the circumferential direction of the outlet. The direction adjustment protrusion is configured at the center of the outlet in the circumferential direction.

11 Claims, 13 Drawing Sheets

ENDOSCOPE EQUIPPED WITH A NOZZLE FOR CLEANING ITS DISTAL END

BACKGROUND OF THE INVENTION

1. Field of the Invention

The present invention relates to an endoscope with a nozzle that is provided at the distal end of the endoscope and ejects gas and/or liquid.

2. Description of the Related Art

An endoscope system includes both the endoscope and a processor. The endoscope is inserted into the body of an examinee so that an internal image can be photographed. The processor is provided outside of the examinee and processes the photographed image. A distal end of the endoscope has an observation port that collects light reflected by an object under observation, and a nozzle that ejects gas or liquid toward the observed object. Gas or liquid ejected from the nozzle removes foreign matter that has adhered to the observation port.

Nozzles that release fluids used for removing foreign matter that adhere to an observation port are disclosed. Japanese Patent No. 3493998 discloses a nozzle with a half-truncated cone-shaped pipe inside that can emit gas or liquid toward the distal end of an endoscope. Japanese Patent No. 3447577 discloses a compacted nozzle that has a tube connected to a fluid ejection port, and the thickness of the wall of the tube on the side of the fluid ejection port is increased. Japanese Patent Application Publication No. H09-201332 discloses a nozzle that moves back and forth so that it approaches an observation port at the moment when fluid is ejected. Japanese Patent No. 3845311 discloses an observation port that is raised from the distal end of an endoscope so as to form a truncated cone, so that fluid flows throughout the whole area of the observation port.

The art disclosed in Japanese Patent No. 3493998, however, increases fluid flow at the center of the stream ejected from the nozzle. Concerning Japanese Patent No. 3447577, however, the diameter of the flow ejected from the nozzle is approximately the same as the diameter of the outlet of the nozzle. Therefore, the diameter of the outlet of the nozzle must be approximately the same as the diameter of the observation port so that the whole surface of the observation port can be cleaned. The nozzle is not compacted in such case, therefore downsizing of an endoscope is inhibited.

Concerning Japanese Patent Application Publication No. H09-201332, however, the construction that allows the nozzle to move back and forth must be added to an endoscope, which inhibits downsizing of an endoscope.

Concerning Japanese Patent No. 3845311, concavities and convexities are formed at the distal end of an endoscope when the observation port is raised from the distal end of the endoscope to form a truncated cone. The concavities and convexities may collect unwanted mucous and tissue residue.

SUMMARY OF THE INVENTION

An object of the present invention is to provide an endoscope that properly cleans an observation port and has a compact fluid-supplying nozzle.

An endoscope is provided having an observation port, a fluid supply pipe, a cap, a fluid ejection channel, and a direction adjustment protrusion. The observation port is provided at the distal end of the endoscope, and collects light reflected from an object. The fluid supply pipe transmits gas and/or liquid to the distal end. The cap blocks the distal end of the fluid supply pipe and is configured so that a partially enclosed semi spherical space is created between the distal end of the fluid supply pipe and the inner surface of the cap. The fluid ejection channel has an outlet in the direction of the observation port, and extends from the edge of the opening at the distal end of the fluid supply pipe to the outlet and occupies the semispherical space inside the cap. The direction adjustment protrusion extends over the outlet in the lengthwise direction of the fluid ejection channel. When the outlet is projected outward toward the observation port, the plane of projection is parallel to the outlet and its lengthwise direction is parallel to the circumferential direction of the outlet. The direction adjustment protrusion is configured at the center of the outlet in the circumferential direction.

BRIEF DESCRIPTION OF THE DRAWINGS

The objects and advantages of the present invention will be better understood from the following description, with references to the accompanying drawings in which.

DESCRIPTION OF THE PREFERRED EMBODIMENTS

Figure 1:
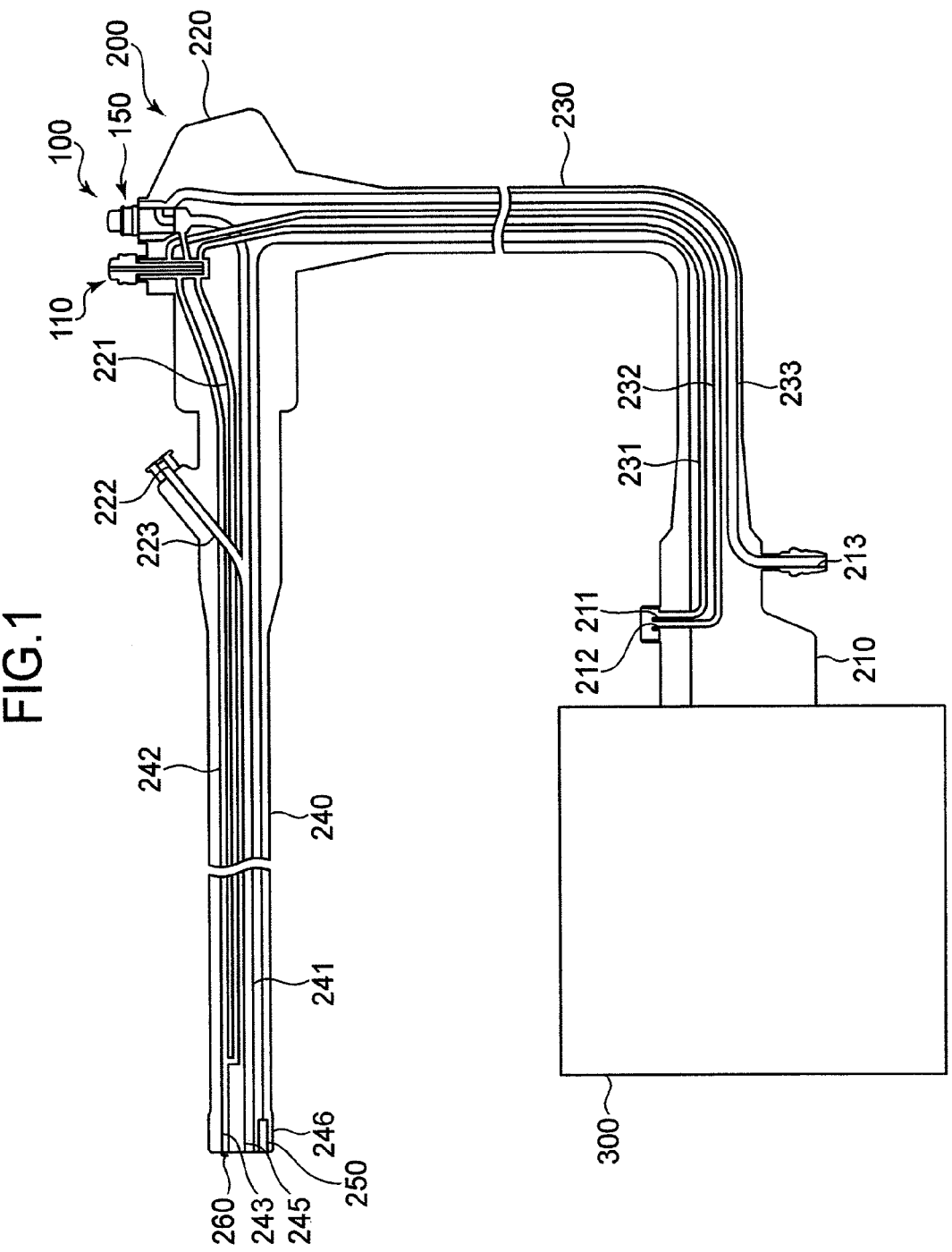
FIG. 1 is a schematic view of an endoscope and a processor according to the first embodiment.

The present invention is described below with references to the embodiments shown in the drawings.

Figure 2:
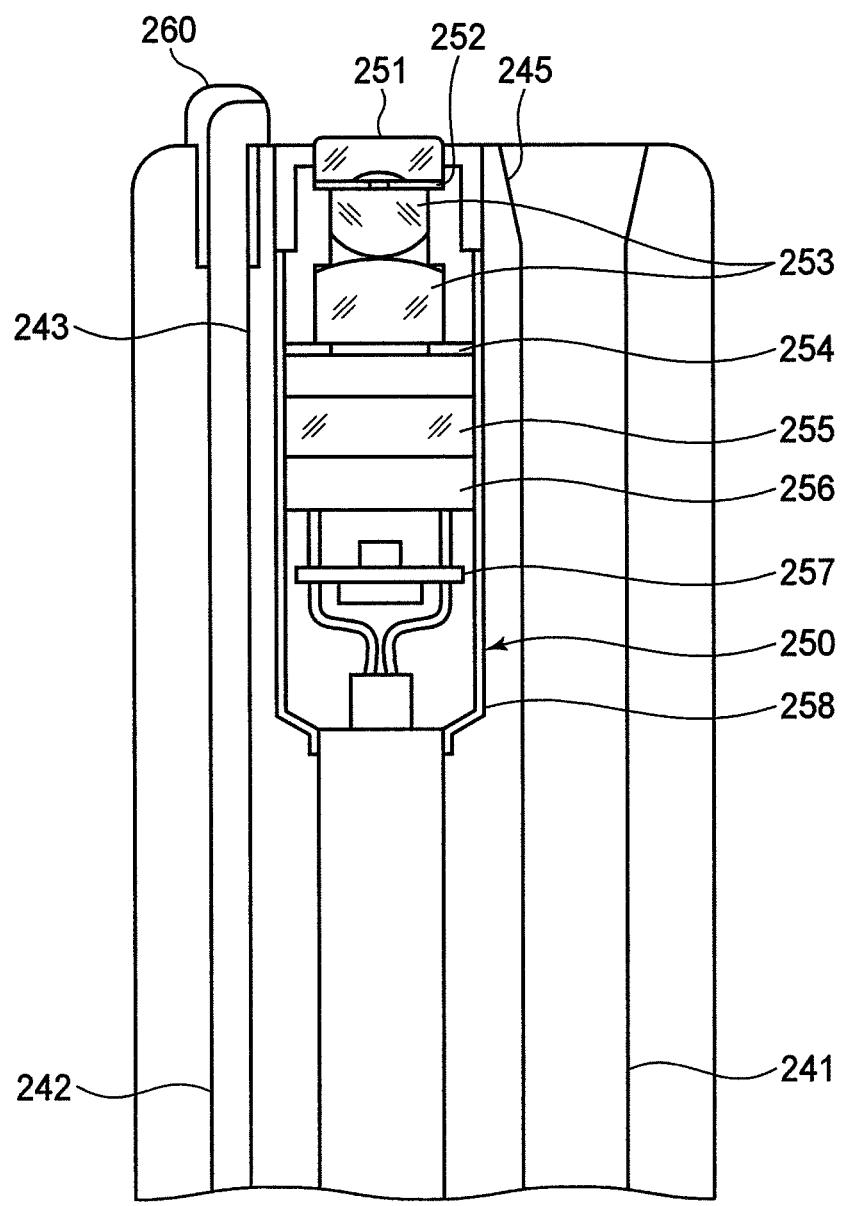
FIG. 2 is a cutaway view from the side of the distal end of the endoscope.
Figure 3:
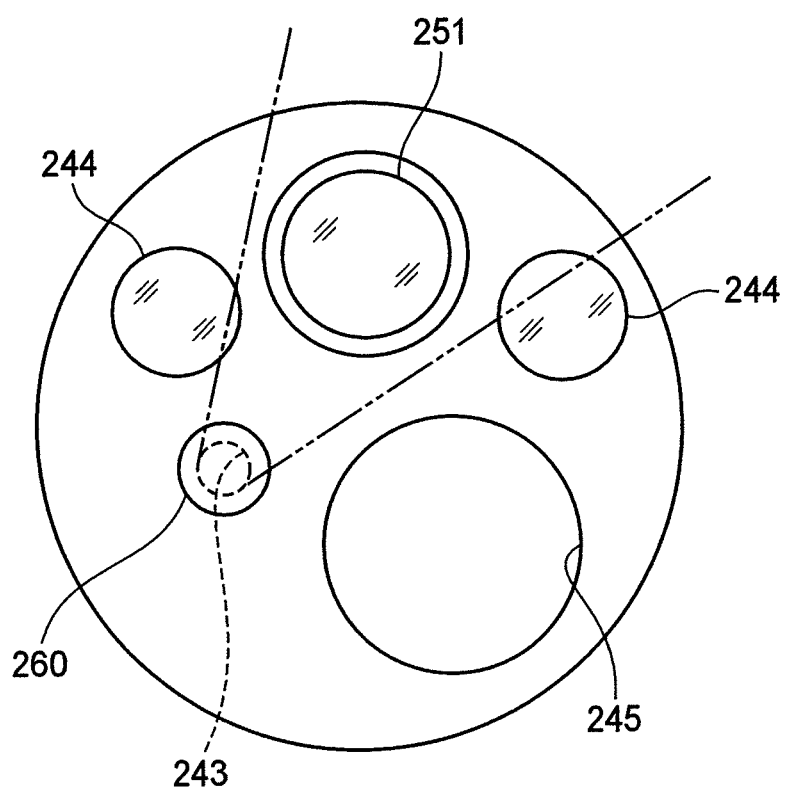
FIG. 3 is a top view of the distal end of the endoscope from its axial direction.

The endoscope system 100 according to the first embodiment is described below with references to FIGS. 1-3. Note that the alignment of each part shown in FIG. 2 is different from that shown in FIG. 3, and a cutaway view of each part shown in FIG. 2 is cut along a plane passing through the center axis of each part.

An endoscope system 100 has the endoscope 200 and a processor 300. The endoscope 200 is inserted into the body of an examinee so that internal images can be photographed. The processor 300 is provided outside of the examinee and processes photographed images.

The endoscope 200 mainly comprises a flexible tube 240 that is inserted into the body of an examinee, an operating part 220 that is held by a user, and a connector 210 that connects the endoscope 220 to the processor 300. A universal cable 230 connects the connector 210 to the operating part 220.

The connector 210 has an air supply opening 211, a liquid supply opening 212, and a negative-pressure supply opening 213. A fluid supply connector running out from a fluid supply tank is connected to the air supply opening 211 and to the liquid supply opening 212 so that gas, e.g. air, can be supplied to the air supply opening 211 and liquid, e.g. water, can be supplied to the liquid supply opening 212. The fluid supply connector and the fluid supply tank are not shown in the figures. The air and water are supplied under predetermined pressures. A negative-pressure connector running out from a negative-pressure pump is connected to the negative-pressure supply opening 213 so as to supply negative pressure. The negative-pressure connector and the negative-pressure pump are not shown in the figures.

A gas supply tube 231 runs from the air supply opening 211 through the connector 210 and the universal cable 230 to the operating part 220. Similarly, a liquid supply tube 232 runs from the liquid supply opening 212 to the operating part 220, and a negative-pressure tube 233 runs from the negative-pressure supply opening 213 to the operating part 220.

The operating part 220 comprises a forceps inlet 222 into which either forceps can be inserted or drugs injected, a fluid switch 110, and a negative-pressure switch 150.

The gas supply tube 231 and the liquid supply tube 232 that run from the connector 210, and the fluid supply pipe 242 and a gas outlet tube 221 that run from the flexible tube 240 are all connected to the fluid switch 110. The gas outlet tube 221 is connected to the fluid supply pipe 242 at the distal end of the flexible pipe 240. The fluid switch 110 comprises a through hole that runs in the push direction. The through hole is connected to the gas supply tube 231 and the fluid supply pipe 242. If the through hole is left open, gas escapes through the through hole from the gas supply tube 231. If the through hole is closed, gas flows into the fluid supply pipe 242 through the gas outlet tube 221 from the fluid supply tube 231. When a user depresses the fluid switch 110, liquid flows to the fluid supply pipe 242 from the liquid supply tube 232. According to these constructions, liquid or gas is ejected from the fluid supply outlet 243 that is provided at the distal end 246 of the flexible tube 240.

The negative-pressure switch 150 is connected to a negative-pressure tube 233 that runs from the connector 210. The negative-pressure switch 150 is a one-step switch, and negative pressure is channeled to a suction tube 241 from the negative-pressure tube 233 when a user depresses the negative-pressure switch 150. According to these constructions, foreign matter are sucked into a suction inlet 245 provided at the distal end 246 of the flexible tube 240.

A forceps tube 223 branches out from the suction tube and is connected to the forceps inlet 222. A plug not shown in the figures is inserted into the forceps inlet 222, and has a slit across the forceps inlet 222 so that gas, liquid, and foreign matter flow into the forceps tube 223 and do not spill out from the forceps inlet 222.

A CCD unit 250, the suction inlet 245, a fluid outlet 243, and a light lens 244 are provided at the distal end 246 of the flexible tube 240. The fluid supply pipe 242 runs from the operating part 220 through the interior of the flexible tube 240 and is connected to the fluid outlet 243. A first fluid nozzle 260 is connected to the opening of the fluid outlet 243. The CCD unit 250 has an observation port 251. The observation port 251 is exposed to the outside of the endoscope at its distal end 246. The suction tube 241 runs from the operation part 220 through the interior of the flexible tube 240 and is connected to the suction inlet 245. The light from the processor 300 passes through the light lens 244, and illuminates an object. The CCD unit 250 photographs an object and then sends an image signal to the processor 300 through a signal cable. Note that the shape of the first fluid nozzle 260 has been simplified in FIG. 2.

The processor 300 sends light to the light lens 244 through a light fiber (not shown in figures), and receives the image signal so that an image can be shown on the display (not shown in figures).

The observation port 251, two light lenses 244, the suction inlet 245 and the first fluid nozzle 260 are all exposed on the end surface of the distal end 246. The two light lenses 244 are provided, one on either side of the observation port 251. The diameter of the fluid outlet 243 is smaller than the diameter of the observation port 251. The outlet of the first fluid nozzle 260 faces the observation port 251. The first fluid nozzle 260 is detachably attached to the endoscope 200.

The construction of the CCD unit 250 is described hereinafter.

The CCD unit 250 mainly comprises the observation port 251, which is a concave lens provided at its front end, a CCD 256, which is an imaging sensor for photographing an object, and a base plate 257 on which peripheral circuitry of the CCD 256 is configured. These components are stored in a casing 258.

An aperture plate 252 is provided on the backside of the observation port 251 and controls both the amount of light entering from the observation port 251 and the depth of field. A field lens 253 is provided at the backside of the aperture plate 252 and brings an object image into focus on the CCD 256. A shield mask 254 and cover glass 255 are provided between the field lens 253 and CCD 256. The shield mask 254 suppresses diffused reflection in a lens barrel to mitigate its influence on a photographed image.

Figure 4:
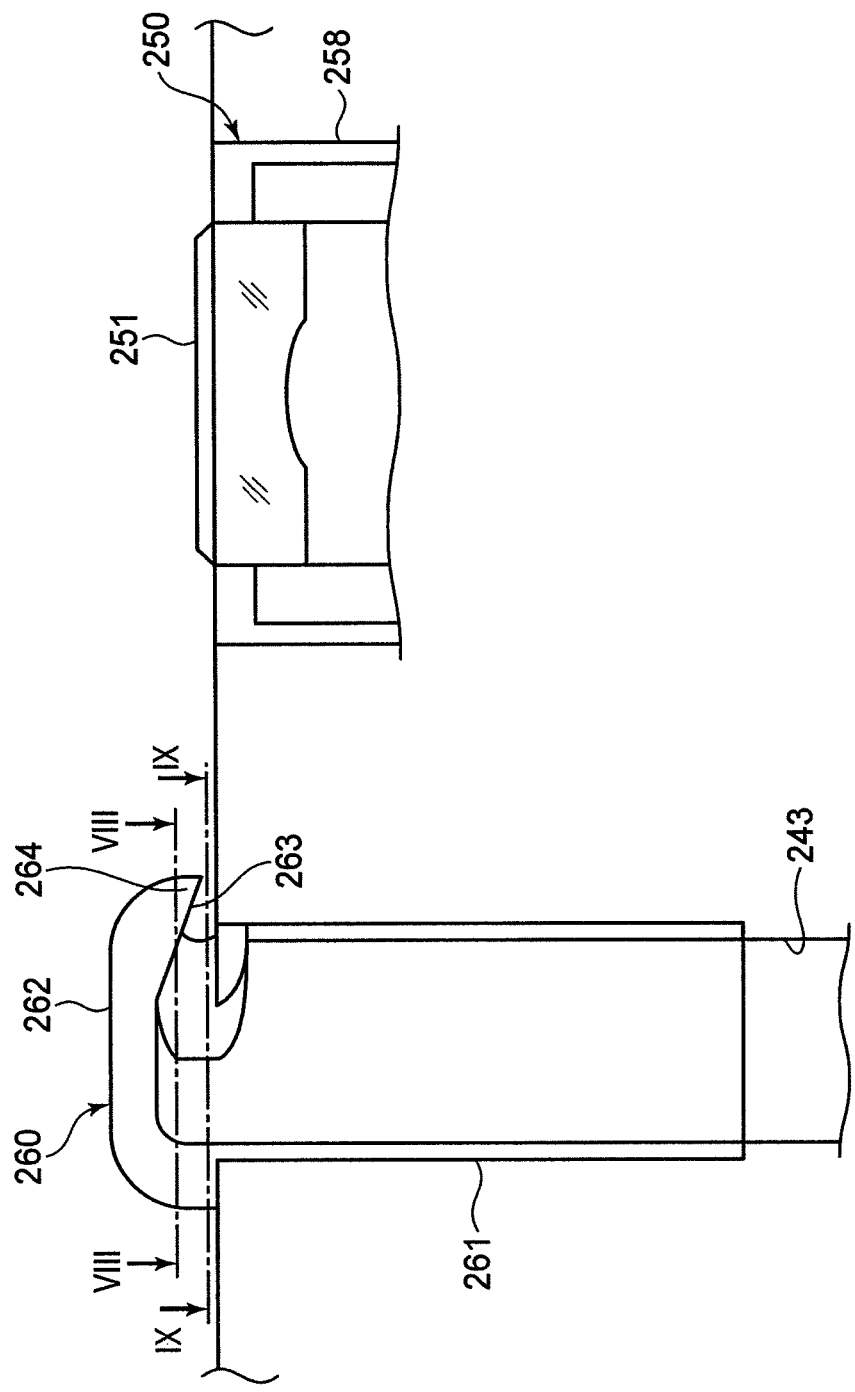
FIG. 4 is a part of a cutaway view of a fluid-supplying nozzle and the observation port.
Figure 5:
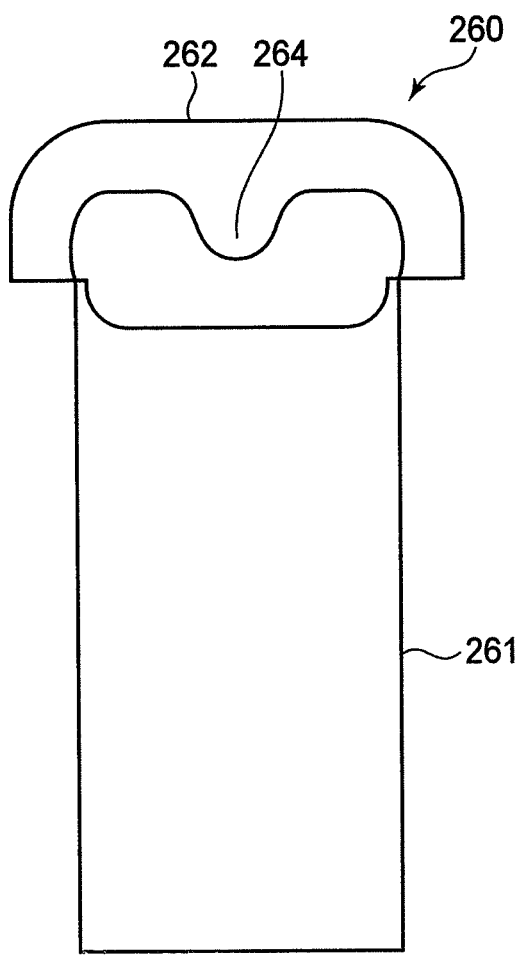
FIG. 5 is a front view of the nozzle.
Figure 6:
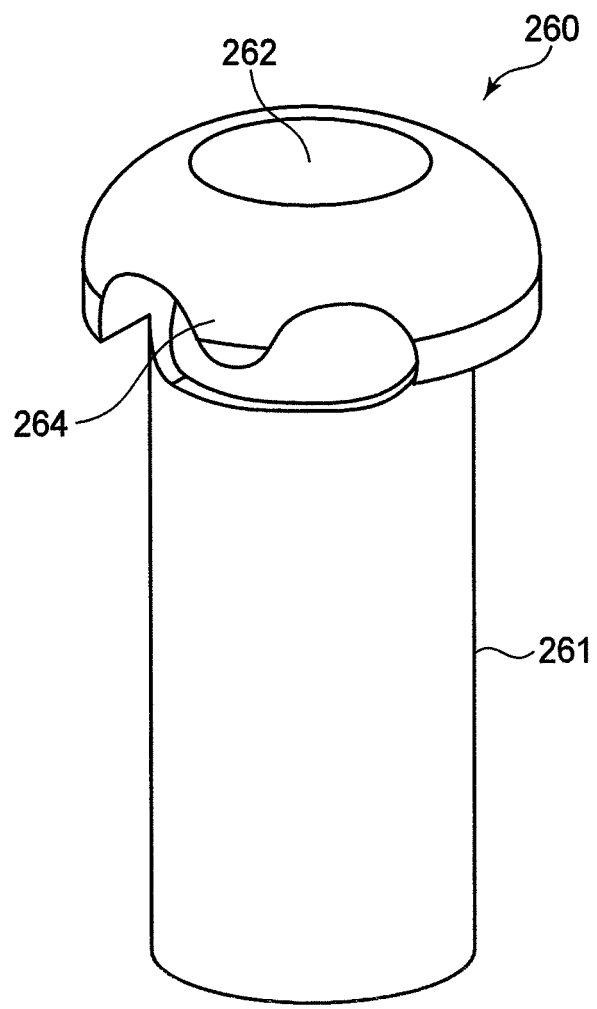
FIG. 6 is a perspective view of the nozzle as seen diagonally from the upper right.
Figure 7:
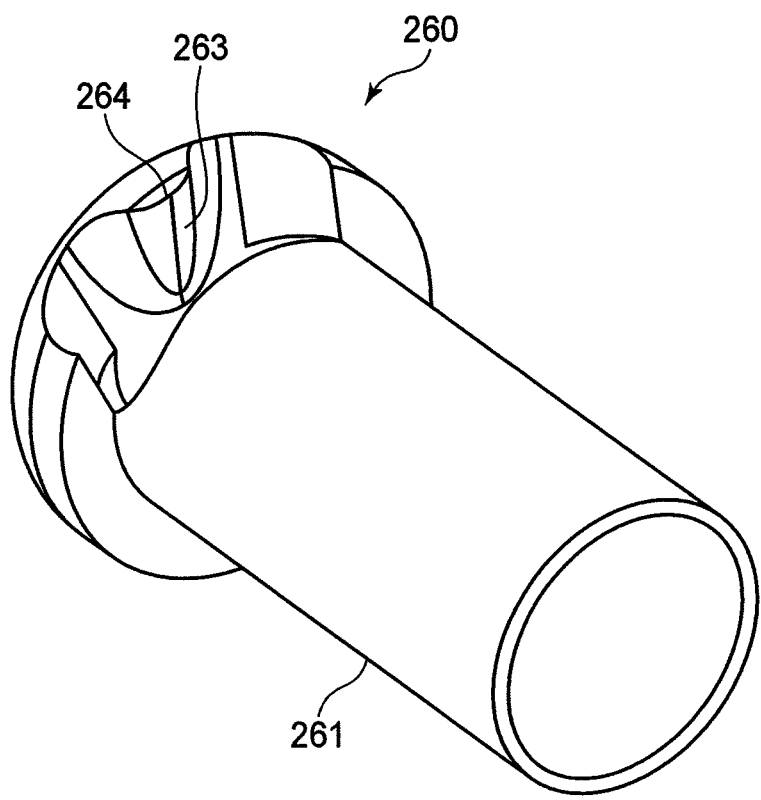
FIG. 7 is a perspective view of the nozzle as seen diagonally from the lower left.
Figure 8:
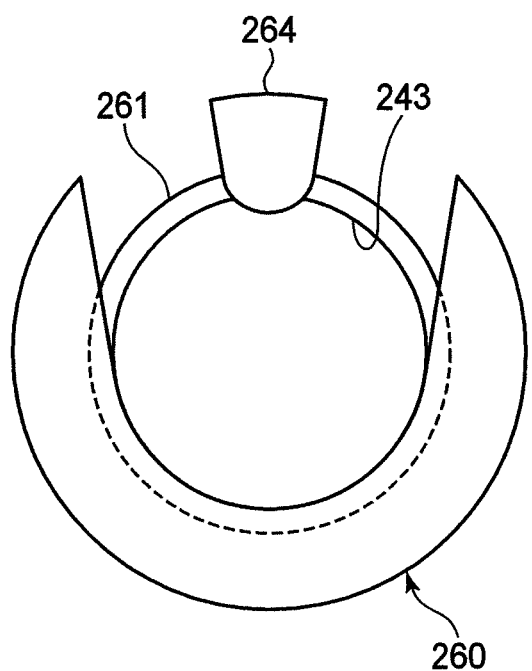
FIG. 8 is a cross-sectional view of the nozzle cut along the line VIII-VIII in FIG. 4.
Figure 9:
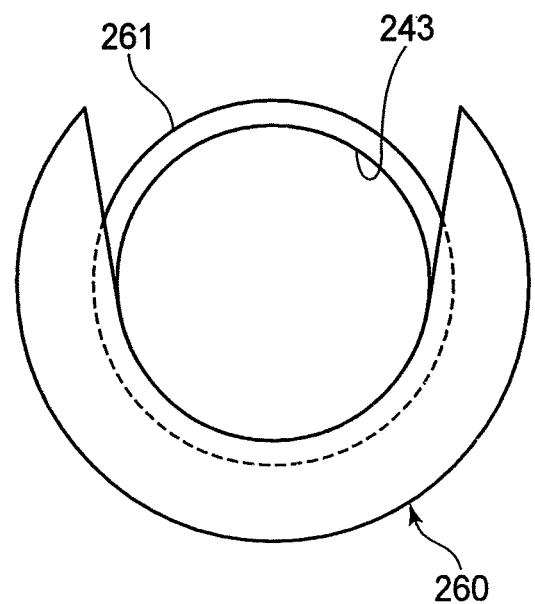
FIG. 9 is a cross-sectional view of the nozzle cut along the line IX-IX in FIG. 4.

The construction of the first fluid nozzle 260 is described hereinafter with references to FIGS. 4-9. Note that, a cutaway view of each part shown in FIG. 4 is cut along a plane passing through the center axis of each part.

The first fluid nozzle 260 comprises a section of first insertion pipe 261 that is cylindrical, a first cap 262 that blocks one end of the first insertion pipe 261, a first fluid ejection channel 263 that is provided between the first cap 262 and the end of the first insertion pipe 261, and a first direction adjustment protrusion 264 that projects from the inner surface of the first fluid ejection channel 263.

The shape of the first insertion pipe 261 is cylindrical such that its external and internal diameters are constant, so that its internal diameter is the same as the internal diameter of the fluid outlet 243 and the fluid supply pipe 242, and its external diameter is larger than the internal diameter of the fluid outlet 243 and the fluid supply pipe 242. A part of the opening of the distal end of the first insertion pipe 261 is U-shaped to form a U-shaped channel.

The first cap 262 is integrally attached to the end surface of the distal end of the first insertion pipe 261 so as to block the opening of the distal end of the first insertion pipe 261 and create a partially enclosed space at the end of the section of first insertion pipe 261.

The first cap 262 is dome-shaped, and the thickness of its wall is the same as the thickness of the wall of the first insertion pipe 261. The center of the top of the dome is flat along the axis of the dome, so as to form a plane. In the first cap 262, the surface facing the fluid outlet 243 is the cap ceiling surface of the first cap 262, and the surface connecting the ceiling surface to the inner surface of the first insertion pipe 261 is the cap side surface of the first cap 262. The first fluid ejection channel 263 is formed so as to run through the cap side surface and open along the radial direction of the first cap 262.

The first fluid ejection channel 263 is formed between a canopy extending from the first cap 262 and the U-shaped channel of the first insertion pipe 261, and is surrounded by a ceiling surface extending from the cap ceiling surface, a side surface extending from the side surface of the dome shape, and a bottom surface extending from the U-shaped portion of the first insertion pipe 261. The canopy has a U-shaped cross section and extends radially outward from the first cap 262.

The width of the first fluid ejection channel 263, i.e. in the direction parallel to the end surface of the section of first insertion pipe 261, is longer than the height of the first fluid ejection channel 263, i.e. in the direction orthogonal to the end surface of the first insertion pipe 261. The width of the first fluid ejection channel 263 is shorter than the diameter of the observation port 251. On the projected plane that is parallel to the outlet of the first fluid ejection channel 263, when the first fluid ejection channel 263 faces toward the observation port 251, the width of the first fluid ejection channel 263 is parallel to the width of the projected plane encompasses the diameter of the observation port 251.

The distance between two side walls that are the side surfaces of the first fluid ejection channel 263 increases with increasing distance from the first cap 262. In other words, the first fluid ejection channel 263 gradually become wider the further it is from the first cap 262. The width of the first fluid ejection channel 263 is less than the diameter of the observation port 251.

The first direction adjustment protrusion 264 projects outward from the top of the first cap 262 and forms an overhang over the first fluid ejection channel 263 that extends radially outward from the axis of the first insertion pipe 261. The first direction adjustment protrusion 264 is provided along the center of the first fluid ejection channel 263. The first direction adjustment protrusion 264 does not make contact with the bottom of the first fluid ejection channel 263, so that a space is created between the bottom of the first fluid ejection channel 263 and the first direction adjustment protrusion 264. The projecting length of the first direction adjustment protrusion 264 extends the farthest downward at the outlet, i.e. at the opening of the first fluid ejection channel 263, and it is shorter the closer it is to the first cap 262. The ceiling and the first direction adjustment protrusion 264 are continuously connected by a rounded surface.

When gas or liquid, e.g. water or air, passes through the fluid supply pipe 242, water or air traveling through the first insertion pipe 261 collide with the ceiling of the first cap 262 before entering the first fluid ejection channel 263. Water or air is deflected toward both nearby side walls of the first fluid ejection channel 263 and flow along the side surfaces of the first fluid ejection channel 263. Therefore, the flow of water or air flowing out from the first fluid ejection channel 263 expands in the width direction of the first fluid ejection channel 263.

The flow of water or air deflected by the ceiling of the first fluid ejection channel 263 collides with the first direction adjustment protrusion 264 so that it is split by the first direction adjustment protrusion 264 and expands in the direction of width of the first fluid ejection channel 263. As described hereinbefore, a space between the bottom of the first fluid ejection channel 263 and the first direction adjustment protrusion 264. Water or air flowing in the space travels in the extending direction of the first fluid ejection channel 263. Therefore, the flow that is created from a fluid that passes underneath the first direction adjustment protrusion 264 when it exits through the outlet of the first fluid ejection channel 263 travels flat along the plane of the surface of the distal end of the first insertion pipe 261 as it moves toward the observation port 251. The first fluid nozzle 260 creates a flow that expands in the lengthwise direction after it is ejected from the first fluid ejection channel 263 to create a wide-ranging uniform water current or air flow that travels flat along the plane of the surface of the distal end of the first insertion pipe 261.

The first fluid nozzle 260 creates a straight flow that ejects from the first fluid ejection channel 263 before expanding in the width direction of the first fluid ejection channel 263, so as to create a uniform water current or air flow over a wide range.

According to such constructions, a uniform water current or air flow is created over a wide range when the first fluid nozzle 260 is miniaturized, so that the first fluid nozzle 260 does not come into the angle of view of the CCD 256, and illumination light does not influence a photographed image by reflection off of the first fluid nozzle 260. Water or air is directed toward the observation port 251 when the ejecting direction of the first fluid nozzle 260 is slightly out of alignment with the regular alignment of the assembly.

Uneven surfaces are not created on the outer surface of the first fluid nozzle 260, so that foreign matter does not adhere to the endoscope 200.

Figure 10:
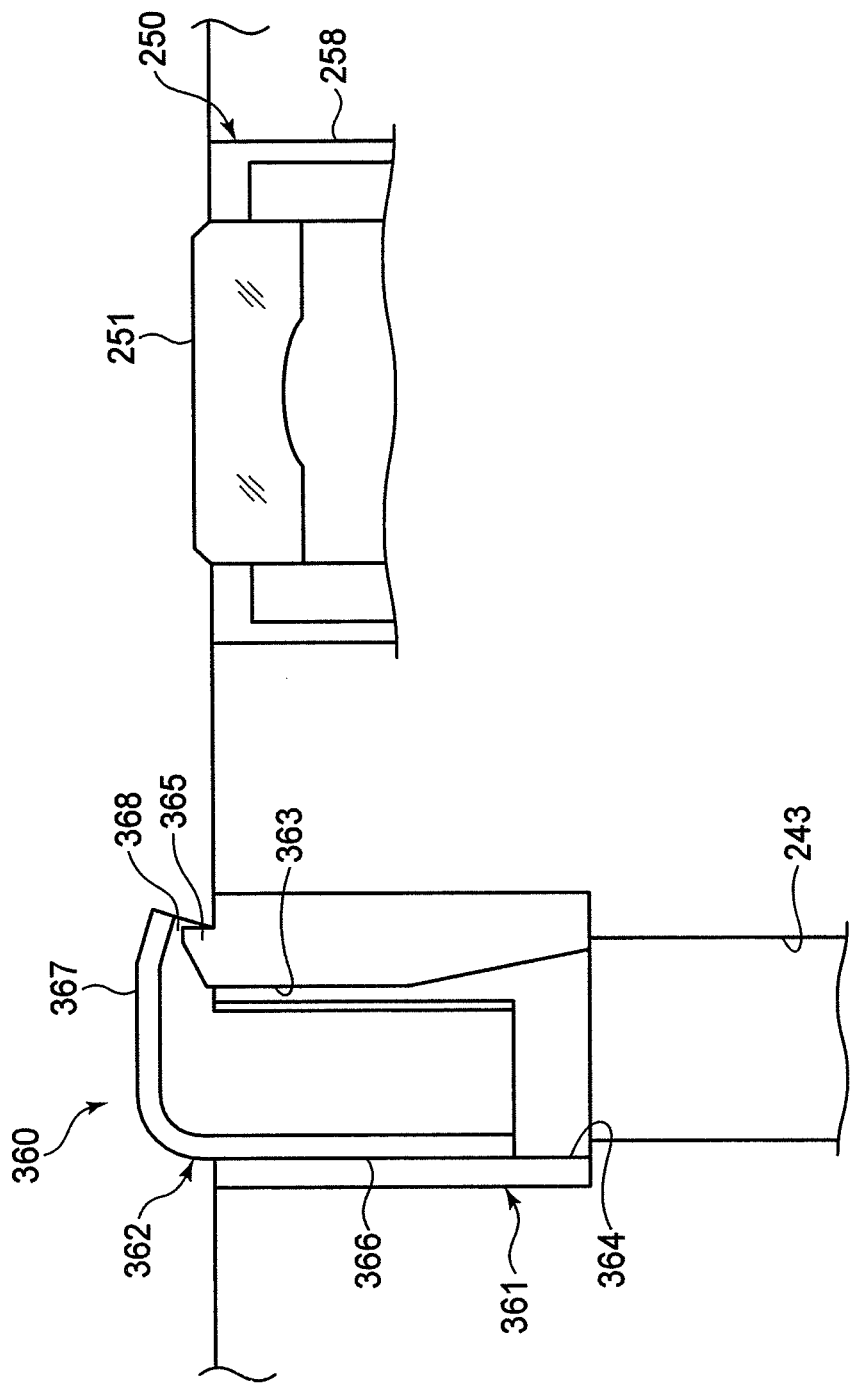
FIG. 10 is a part of a cutaway view of a nozzle and an observation port according to the second embodiment.
Figure 11:
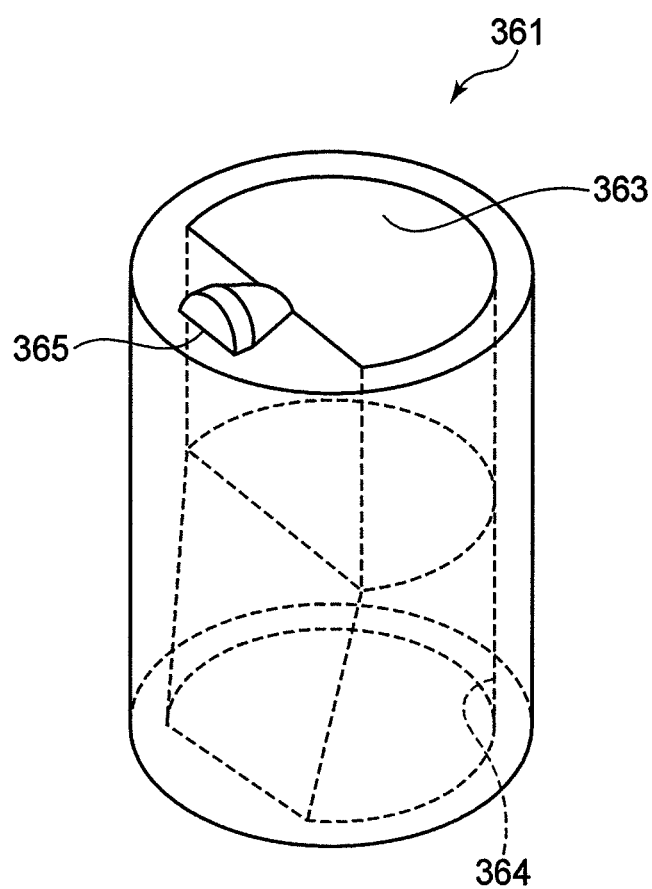
FIG. 11 is a perspective view of an insertion pipe.
Figure 12:
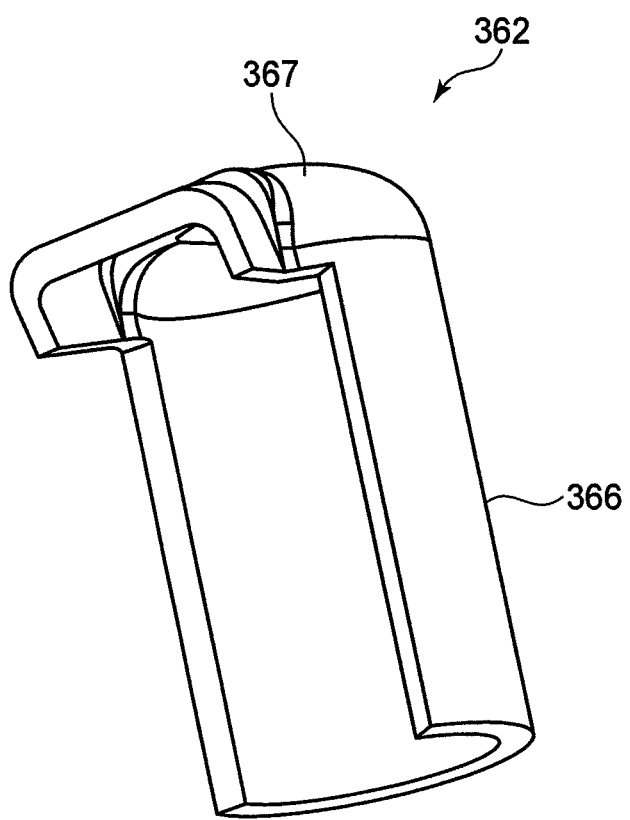
FIG. 12 is a perspective view of a guide.

The construction of the endoscope system 100 according to the second embodiment is described hereinafter with reference to FIGS. 10-12. The constructions of the second embodiment that are similar to the first embodiment have the same numeral applied and their descriptions have been omitted. Note that, a cutaway view of each part shown in FIG. 10 is on a plane passing through a center axis of each part.

The constructions of the endoscope 200 and the processor 300 are similar to the first embodiment; however, the shape of the fluid nozzle differs to the first embodiment. Therefore, the second fluid nozzle 360 according to the second embodiment is described hereinafter.

The second fluid nozzle 360 comprises a second of insertion pipe 361, which is substantially cylindrical, and a guide 362.

The second insertion pipe 361 is formed by resin molding and has cylinder-shaped outer lateral surface. The diameter of the outer lateral surface is greater than the internal diameter of the fluid outlet 243.

The inner lateral surface of the second insertion pipe 361 comprises an upper inner surface 363 and a lower inner surface 364. When the second fluid nozzle 360 is attached to the endoscope 200, the upper inner surface 363 is located near the distal end and the lower inner surface 364 is located near the proximal end.

The upper inner surface 363 has a shape that is formed by cutting a cylinder with a plane that is parallel to the axis of the cylinder, so that the upper inner surface 363 is a semicircle formed by a curved surface that is a part of the cylinder and a rectangle plane. The cross sections of the upper inner surface 363 cut by planes orthogonal to the axis are the same. The upper inner surface 363 take on a tunnel shape at the distal end of the second insertion pipe. The tunnel shape is formed by an arc that is a part of the curved surface of the cylinder and a chord that is a part of a rectangular plane.

The lower inner surface 364 has a shape that is formed by cutting a cylinder with a plane that is not parallel to the axis of the cylinder, so that the lower inner surface 364 is formed by a curved surface that is a part of the cylinder and a trapezoidal plane. The long side of the trapezoid overlaps one side of the rectangle that forms the upper inner surface 363. The short side of the trapezoid is located on the proximal end of the second insertion pipe 361. The curved surface of the upper inner surface 363 and the lower inner surface 364 has the same diameter and forms a continuous curve. In other words, at the section where the upper inner surface 363 and the lower inner surface 364 are joined together, the cross sections of the upper inner surface 363 and the lower inner surface 364 cut by a plane perpendicular to the axis of the cylinder are the same. The cross sections of the upper inner surface 363 cut by planes orthogonal to the axis are the same. The lower inner surface 364 takes on a tunnel shape at the proximal end of the second insertion pipe. The tunnel shape is formed by an arc that is a part of the curved surface of the cylinder and a chord that is a part of a rectangular plane. The cross sections of the lower inner surface 364 cut by planes orthogonal to the axis are homothetic.

The second direction adjustment protrusion 365 is provided on the distal end surface of the second insertion pipe 361. The shape of the second direction adjustment protrusion 365 is a combination of a truncated cone and a cylinder that are connected so that their axes coincide with one another, and then the truncated cone and the cylinder are bisected by a plane that includes both axes. The diameter of the shared surface of the truncated cone and the diameter of the shared surface of the cylinder are the same. The shared surface of the truncated cone is connected to the shared surface of the cylinder.

The plane of the second direction adjustment protrusion 365 that bisects both the truncated cone and the cylinder is the plane of the distal end surface of the second insertion pipe 361. Therefore, the axis of the second direction adjustment protrusion 365 is located on the distal end surface of the second insertion pipe 361. The second direction adjustment protrusion 365 is located on the distal end surface of the second insertion pipe 361 so that the axis of the second direction adjustment protrusion 365 orthogonally intersects with the center of the chord of the upper inner surface 363. The chord intersecting the axis appears on the distal end surface of the insertion pipe 361. The top of the truncated cone is flush with the rectangle plane of the upper inner surface 363.

The guide 362 is formed by sheet metal processing, and comprises the support 366 and the second cap 367.

The support 366 has a shape that is formed by cutting a cylinder that has constant thickness with a plane that is parallel to the axis of the cylinder. Therefore, the support 366 is C-shaped on its cross-sectional plane that is orthogonal to the axis of the cylinder. The cross sections of the support 366 cut by planes orthogonal to the axis are the same. The diameter of the outer surface of the support 366 is substantially the same as the diameter of the upper inner surface 366.

Concerning the support 366, the distance between the axis of the cylinder and the plane cutting through the cylinder is shorter than the distance between the axis and the plane cutting through the upper inner surface 363. In other words, the interior angle of the circular arc cut away from the support 366 is larger than the interior angle of the circular arc cut away from the upper inner surface 363. Therefore, the cut surface of the support 366 does not make contact with the upper inner surface 363.

The second cap 367 is dome-shaped and the thickness of its wall is the same as the thickness of the wall of the support 366. The top of the dome shape is slightly flat along the axis of the dome, so as to form a plane. The second cap 367 is attached to the support 366 so as to block the opening of the distal end of the support 366 and create a partially enclosed space outside of the opening. In the side wall of the second cap 367, a second fluid ejection channel 368 is created that opens outward in the radial direction.

The second fluid nozzle 360 is created by inserting the support 366 into the upper inner surface 363. The construction of the guide 362 inserted into the second insertion pipe 361 is described hereinafter.

The second fluid ejection channel 368 is formed between a canopy extending from the second cap 367 and the distal end surface of the second insertion pipe 361. The canopy has a U-shaped cross section and extends radially outward from the second cap 367. The width of the second fluid ejection channel 368, i.e. the length in the direction parallel to the end surface of the second insertion pipe 361, is longer than the height of the second fluid ejection channel 368, i.e. the length in the direction orthogonal to the end surface of second inserting pipe 361. On the projected plane that is parallel to the outlet of the second fluid ejection channel 368, when the second fluid ejection channel 368 faces toward the observation port 251, the width of the projected plane encompasses the diameter of the observation port 251.

The canopy is angled downward toward the distal end surface of the second insertion pipe 361. In other words, the width of the second fluid ejection channel 368 decreases with increasing distance away from the second cap 367. The distance between the two side walls of the canopy that are the side surfaces of the second fluid ejection channel 368 increases with increasing distance from the second cap 367. In other words, the width of the second fluid ejection channel 368 increases with increasing distance from the second cap 367. The width of the second fluid ejection channel 368 is less than the diameter of the observation port 251.

The second direction adjustment protrusion 365 projects between the canopy and the distal end surface of the second insertion pipe 361. The second direction adjustment protrusion 365 is provided at the center of the first fluid ejection channel 263 within the width of the second fluid ejection channel 368. The second direction adjustment protrusion 365 does not make contact with the ceiling of the canopy, so that a space is created between the second direction adjustment protrusion 365 and the ceiling of the canopy.

When gas or liquid, e.g. water or air, is sent through the fluid supply pipe 242, water or air flows through the second insertion pipe 361 to the guide 362. And then, water or air collides with the cap ceiling of the second cap 367 and is deflected into the second fluid ejection channel 368. Water or air flowing near the center of the second fluid ejection channel 263 is channeled along the side walls of the canopy. Therefore, water or air flowing out from the second fluid ejection channel 368 expands in the direction of the width of the second fluid ejection channel 368.

Water or air flowing near the center of the second fluid ejection channel 368 separates when it collides with the second direction adjustment protrusion 365 before expanding in the direction of the width of the second fluid ejection channel 368. As described hereinbefore, a space is created between the ceiling of the canopy and the second fluid ejection channel 365. Water or air flowing in the space straightly travels in the extending direction of the second fluid ejection channel 368. Therefore, the straight flow is created and ejected from the second fluid ejection channel 368.

The second fluid nozzle 360 creates a straight flow that ejects from the second fluid ejection channel 368 before expanding in the width direction of the second fluid ejection channel 368, so as to create a uniform water current or air flow over a wide range.

According to such constructions, a uniform water current or air flow is created over a wide range when the second fluid nozzle 360 is miniaturized, so that the first fluid nozzle 360 does not come into the angle of view of the CCD 256, and a photographed image is not influenced by reflection off of the second fluid nozzle 360. Water or air is directed toward the observation port 251 when the ejecting direction of the second fluid nozzle 360 is slightly out of alignment with the regular alignment of the assembly.

The second direction adjustment protrusion 365 can be replaced by replacing the second insertion pipe 361 because the second insertion pipe 361 is integrally molded using resin with the second direction adjustment protrusion 365, which allows for easy maintenance of the endoscope 200.

The production of the guide 362 is less complicated and less expensive than processing by cutting because the guide is made by sheet metal processing. The second direction adjustment protrusion 365 is formed on the second insertion pipe 361, so that uneven surfaces are not created on the outer surface of the canopy and foreign matter does not adhere to the endoscope 200.

Note that, the second insertion pipe may be made by other processing methods.

The second direction adjustment protrusion 365 may be formed directly on the distal end surface of the endoscope 200 without the second insertion pipe 361.

The guide may be made by another processing method other than sheet metal processing.

The height of the second fluid ejection channel 368 may not increase with increasing distance from the second cap 367. In other words, the height of the second fluid ejection channel 368 may be constant from the height of the second cap 367.

Figure 13:
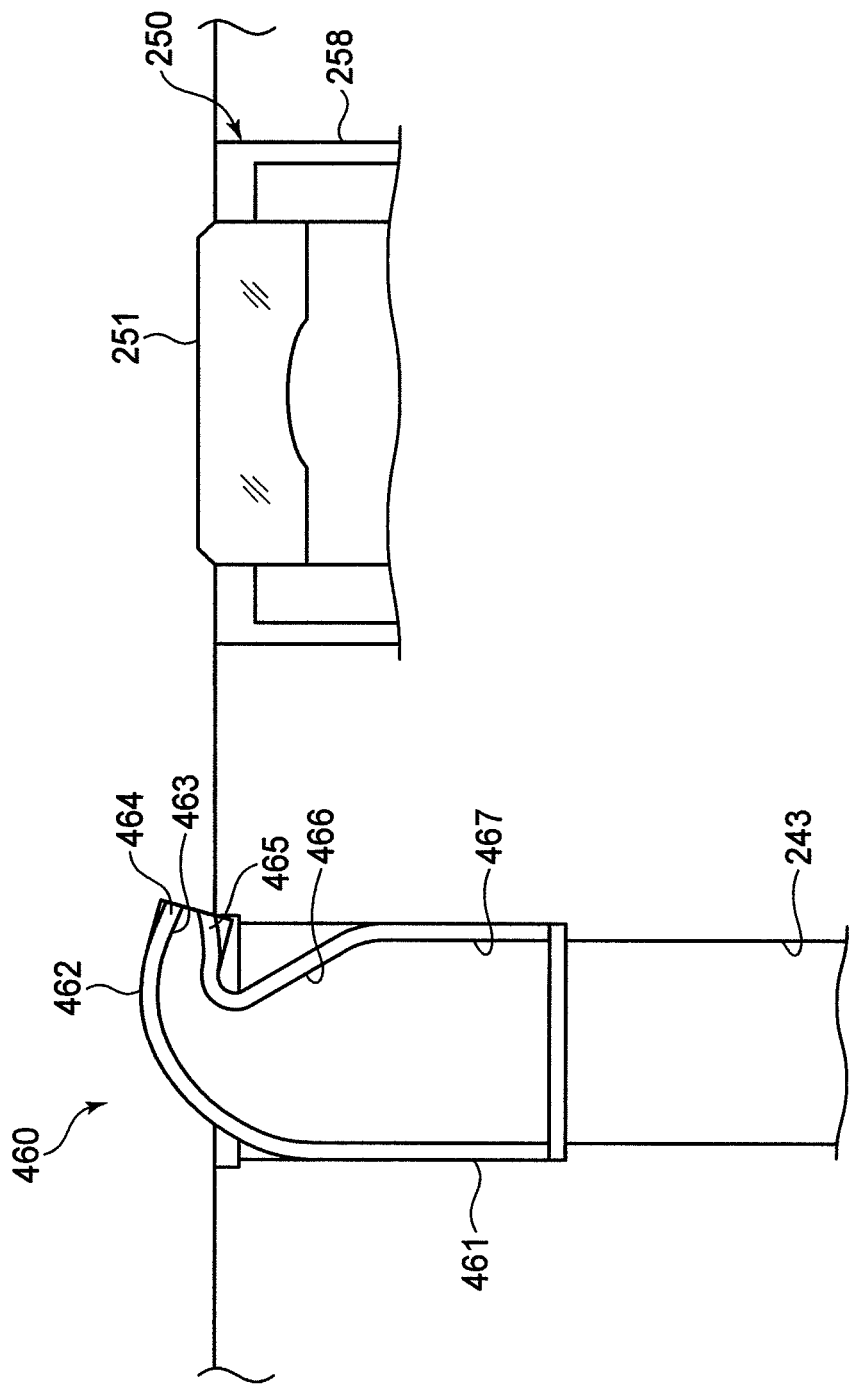
FIG. 13 is a part of a cutaway view of a nozzle and an observation port according to the third embodiment.
Figure 14:
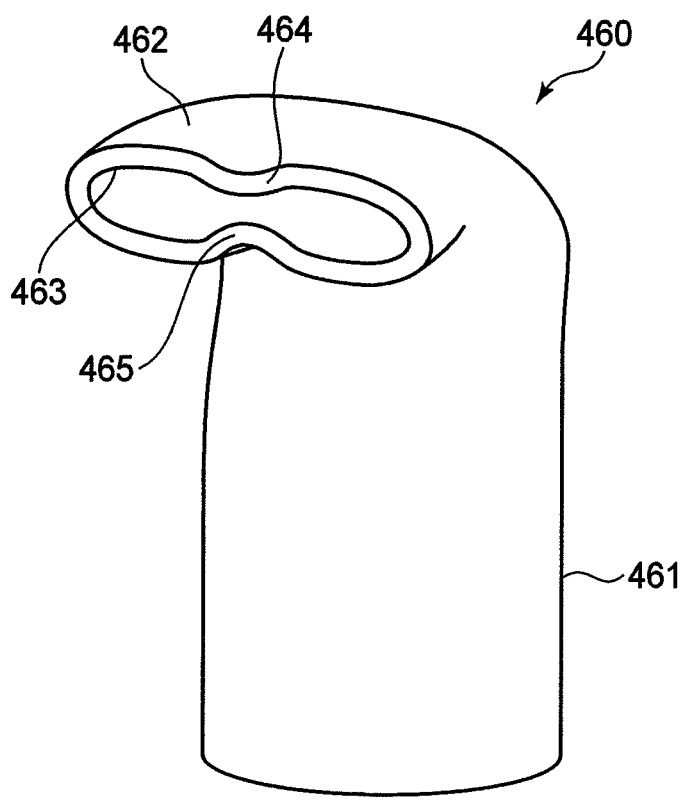
FIG. 14 is a perspective view of the nozzle.

The construction of the endoscope system 100 according to the third embodiment is described hereinafter with reference to FIGS. 13 and 14. The constructions of the third embodiment that are similar to the first embodiment have the same numeral applied and their descriptions have been omitted. Note that, a cutaway view from the side of each part shown in FIG. 13 is on a plane passing through a center axis of each part.

The constructions of the endoscope 200 and the processor 300 are similar to the first embodiment; however, the shape of the fluid nozzle is different from the first embodiment. Therefore, the third fluid nozzle 460 according to the third embodiment is described hereinafter.

The third fluid nozzle 460 is made by forming a tube that comprises a third insertion pipe 461, a third cap 462, and a third fluid ejection channel 463.

The third insertion pipe 461 has a cylinder-shaped outer lateral surface. The diameter of the outer lateral surface is greater than the internal diameter of the fluid outlet 243. The inner lateral surface of the third insertion pipe 461 comprises an upper inner surface 466 and a lower inner surface 467. When the third fluid nozzle 460 is attached to the endoscope 200, the upper inner surface 466 is positioned near the distal end, and the lower inner surface 467 is located near the proximal end.

The upper inner surface 466 is tapered so that its cross-sectional area decreases the closer it is to the distal end. The lower inner surface 467 is the interior surface of a cylinder.

The third cap 462 is made by bending a tube so as to make a continuous arc from the third insertion pipe 461 that blocks the opening at the distal end of the third insertion pipe 461 and creates a partially enclosed space at the end of the opening. The end of the bended tube configured similar to a FIG. 8 lying on its side that has two ellipses instead of two circles as its end shapes.

The shape of the third fluid ejection channel 463 is similar to an elliptical tunnel that includes a ceiling that extends down from the third cap 462 and is integrated with rounded sidewalls that extend further down and are integrated with a floor at the bottom of the tunnel.

The width, i.e. the length of the third fluid ejection channel 463 in the direction parallel to the end surface of the third insertion pipe 461 is longer than the height, i.e. the length of the third fluid ejection channel 463 in the direction orthogonal to the end surface of the third insertion pipe 461. The width of the third fluid ejection channel 463 is shorter than the diameter of the observation port 251. On the projected plane that is parallel to the outlet of the third fluid ejection channel 463, when the third fluid ejection channel 463 faces toward the observation port 251, the width of the projected plane encompasses the diameter of the observation port 251.

In the center of the ceiling, the third direction adjustment protrusion 464 projects downward into the third fluid ejection channel 463. In the center of the floor, the fourth direction adjustment protrusion 465 projects upward into the third fluid ejection channel 465. The third direction adjustment protrusion 464 does not make contact with the fourth direction adjustment protrusion 465, so that a space is created between the third direction adjustment protrusion 464 and the fourth direction adjustment protrusion 465. The downward and upward projecting lengths of the third and fourth direction adjustment protrusions 464 and 465, respectively, are longest at the outlet, i.e. the opening of the third fluid ejection channel 463, and are shortest closest to the third cap 462.

When gas or liquid, e.g. water or air, is sent through the fluid supply pipe 242, water or air collide with the cap ceiling of the third cap 462 of the third insertion pipe 461, and is directed into the third fluid ejection channel 463. Water or air flowing near the center of the third fluid ejection channel 463 collide with the third direction adjustment protrusion 464 and the fourth direction adjustment protrusion 465 so that it becomes split by the third and fourth direction adjustment protrusions 464 and 465, and expands in the direction of width of the third fluid ejection channel 463. As described hereinbefore, a space is created between the third direction adjustment protrusion 464 and the fourth direction adjustment protrusion 465. Water or air flowing in the space goes straight along the extending direction of the third fluid ejection channel 468. Therefore, the straight flow is created that ejects directly from the third fluid ejection channel 463.

The third fluid nozzle 460 creates flow by ejecting fluid directly from the third fluid ejection channel 463, and the flow extending in the direction of width of the third fluid ejection channel 463 creates uniform water current or air flow over a wide range.

According to such constructions, uniform water current or air flow is created over a wide range when the third fluid nozzle 460 is miniaturized, so that the third fluid nozzle 460 does not come into the angle of view of the CCD 256 and illumination light does not influence a photographed image by reflection off of the third fluid nozzle 460. Water or air is directed toward the observation port 251 when the direction of ejection of the third fluid nozzle 460 is slightly out of alignment with the regular alignment of the assembly.

Note that, the imaging sensor is not limited to the CCD 256.

Although the embodiment of the present invention has been described herein with references to the accompanying drawings, obviously many modifications and changes may be made by those skilled in the art without departing from the scope of the invention.

The present disclosure relates to subject matter contained in Japanese Patent Application No. 2009-190978 (filed on Aug. 20, 2009), which is expressly incorporated herein, by reference, in its entirety.

What is claimed is:

1. An endoscope comprising:
   an observation port that is provided at a distal end of said endoscope, and collects light reflected from an object;
   a fluid supply pipe that transmits gas and/or liquid to a distal end thereof;
   a cap that blocks the distal end of said fluid supply pipe and is configured so that a partially enclosed semispherical space is created between the distal end of said fluid supply pipe and an inner surface of said cap;
   a fluid ejection channel that has an outlet facing said observation port, and extends from an edge of an opening at the distal end of said fluid supply pipe to the outlet and occupies the semispherical space inside said cap; and
   a direction adjustment protrusion that extends over the outlet in a lengthwise direction of said fluid ejection channel, wherein
   when the outlet faces said observation port, a plane of projection projecting toward said observation port is parallel to the outlet and a lengthwise direction of the plane of projection is parallel to a circumferential direction of the outlet,
   said direction adjustment protrusion is configured at a center of said outlet in the circumferential direction, and
   a downward projected length of said direction adjustment protrusion continuously increases in the lengthwise direction of said fluid ejection channel toward the outlet, such that said direction adjustment protrusion extends toward a center of the fluid ejection channel.

2. The endoscope according to claim 1, wherein a length of said fluid ejection channel in the lengthwise direction increases from the edge of the opening at the distal end of said fluid supply pipe toward the outlet.

3. The endoscope according to claims 1, wherein the outlet is projected outward toward said observation port onto the plane of projection that is parallel to the outlet, the length of the outlet in the lengthwise direction is less than a diameter of said observation port.

4. The endoscope according to claim 1, wherein a length of the direction adjustment protrusion increases in the lengthwise direction from the fluid ejection channel toward the outlet.

5. The endoscope according to claim 1, wherein the direction adjustment protrusion projects from an inner surface of the outlet, and the inner surface is opposite to the opening at the distal end of said fluid supply pipe.

6. The endoscope according to claim 5, wherein the downward projected length of the direction adjustment protrusion increases from a ceiling plane of said cap to the outlet, and the ceiling plane faces the opening of the distal end of said fluid-supplying pipe.

7. The endoscope according to claim 6, further comprising a support pipe that is inserted into an inner surface of said fluid supply pipe, and wherein said cap is integrated with said support pipe and covers an opening of the distal end of said support pipe, said fluid ejection channel is integrated with said support pipe and extends from an opening edge of the distal end of said support pipe to an outside of said cap, and said direction adjustment protrusion is integrated with said fluid ejection channel.

8. The endoscope according to claim 1, wherein the direction adjustment protrusion projects from an inner surface of the outlet, and the inner surface faces the opening at the distal end of said fluid supply pipe.

9. The endoscope according to claim 8, further comprising an insertion pipe that is inserted into an inner surface of said fluid supply pipe, and wherein said cap covers an opening at a distal end of said insertion pipe, said fluid ejection channel is defined by said cap and a top surface of the distal end that is provided around the opening of the distal end of said insertion pipe, said direction adjustment protrusion is integrated with the top surface of said fluid ejection channel.

10. The endoscope according to claim 1, wherein the direction adjustment protrusion projects from an inner surface of the outlet, and the inner surface is opposite to the opening at the distal end of said fluid supply pipe, and the direction adjustment protrusion projects from the inner surface of the outlet, and the inner surface faces the opening at the distal end of said fluid supply pipe.

11. The endoscope according to claim 10, further comprising a support pipe that is inserted into an inner surface of said fluid supply pipe, and wherein said cap is integrated with said support pipe and covers an opening at a distal end of said support pipe, said fluid ejection channel is integrated with said support pipe and extends from an opening edge of the distal end of said support pipe to an outside of said cap, and said direction adjustment protrusion being defined by said fluid ejection channel in an inner radial direction so as to be integrated with said fluid ejection channel.

* * * * *